United States Patent [19]

Hoffmann et al.

[11] 4,012,465
[45] Mar. 15, 1977

[54] ALKYL AND CYCLOALKYL METHYLPHOSPHONOFLUORIDOTHIOATES

[75] Inventors: Friedrick Wilhelm Hoffmann; Ray Rei Irino, both of Bel Air, Md.

[73] Assignee: The United States of America as represented by the Secretary of the Army, Washington, D.C.

[22] Filed: Nov. 13, 1962

[21] Appl. No.: 237,407

[52] U.S. Cl. .......................... 260/958; 260/543 P; 260/960; 424/221

[51] Int. Cl.$^2$ ........................................ C07F 9/20

[58] Field of Search ............... 260/461.105, 543 P, 260/958, 960

[56] References Cited
OTHER PUBLICATIONS

Ballreich et al., Chem. Ber. 95, pp. 199 to 202 (1962).

*Primary Examiner*—Leland A. Sebastian
*Attorney, Agent, or Firm*—Nathan Edelberg; Kenneth P. Van Wyck

EXEMPLARY CLAIM

1. A compound having the structure represented by the formula:

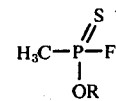

in which R is selected from the group consisting of alkyl groups of 1–5 carbon atoms and cycloalkyl groups of 6–9 carbon atoms.

4 Claims, No Drawings

ALKYL AND CYCLOALKYL METHYLPHOSPHONOFLUORIDOTHIOATES

The invention described herein may be manufactured or used by or for the Government, for governmental purposes, without payment to us of any royalty thereon.

This invention relates to a new series of compounds which may be described as O-alkyl and O-cycloalkyl methyl phosphonofluoridothioates having the flowing formula.

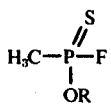

where R is an alkyl group of 1–5 carbon atoms or a cycloalkyl group of 6–9 carbon atoms.

These can also be named as alkyl and cycloalkyl methylthionophosphonic acid fluorides or the corresponding methylfluorothiophosphonates. These compounds have been found to be highly toxic to warm-blooded animals and therefore useful as war gases.

The starting material, methylphosphonothioic dichloride, for the preparation of these compounds is a known compound having been disclosed by Hoffmann et al., J. Am. Chem. Soc. Vol. 80, pg, 3947, Aug. 5, 1948.

The preparation of the new compounds from the above starting material consists of reacting the starting material with hydrogen fluoride gas in the absence of moisture. The methylphosphonothioic difluoride thus prepared is then treated with the selected alkyl alcohol in an inert solvent in the presence of an organic base to produce the alkyl methylphosphonofluoridothioates of this invention.

It is known in the thiophosphate series of compounds that changing the compound from one having a thiono sulfur to one having a thiolo sulfur results in increased toxicity to warmblooded animals (Topley, Chemistry and Industry Dec. 30, 1950, page 5–863). We have made the surprising discovery that in the thiophosphonate compounds of this invention — just the opposite is true.

Compounds such as O,O-dialkyl phosphorofluoridothioates are known to be useful insecticides with low toxicity to warm-blooded aminals. We have now found analogs of these compounds which have the required high toxicity.

EXAMPLE 1

METHYLPHOSPHONOTHOIC DIFLUORIDE

Hydrogen fluoride (83.0 g.) was bubbled slowly into 275.0 g. of methylphosphonothoic dichloride stirred in a cooper flask equipped with a Dry-Ice-trichloroethylene cooled condenser and protected from atmospheric moisture by a drying tube packed with sodium fluoride and calcium chloride. After standing overnight, tributylamine was added to slight alkalinity and the mixture was transferred into a pyrex flask and distilled twice through a glass distillation head to yield 148.0 g. (69.2%) of methylphosphonothioic difluoride, (I) b. p. 63°–63.5° C., which fumes on contact with air.

Analysis: calcd. for $CH_3 F_2 PS$: C, 10.35; H, 2.61; P, 26.69; S, 27.63. Found: C, 10.5; H, 2.7; P, 27.3; S, 27.4.

EXAMPLE 2

O-METHYL METHYLPHOSPHONOFLUORIDE-THIOATE

A mixture of 11.31 g. (0.353 mole) methanol and 35.72 g. (0.353 mole) triethylamime was added from a dropping funnel to 40.97 g. (0.353 mole) of I (prepared by the method set forth in Example 1) in 100 ml. of methylene dichloride. The reaction proceeded exothermically and was stirred for 1 hour. The mixture was stirred for an additional hour until room temperature was reached. The organic layer was washed with three 50 ml portions of water. After drying the organic layer over Drierite, the solvent was stripped and the residue distilled in vacuo to yield 14.6 g. (32.3%) O-methyl methylphonofluoridothionate b.p. 66°–68° C. at 105 mm.

Analysis: Calcd for $C_2 H_6 FOPS$: C, 18.75; H, 4.72; F, 14.83; P, 24.18. Found: C, 19.03; H, 4.71; F, 14.18; P, 24.28.

EXAMPLE 3

O-ISOPROPYL METHYLPHOSPHONOFLUORIDETHIOATE

A solution of 12.02 g. (0.20 mole) of isopropanol and 20.24 g. (0.20 mole) of triethylamine was added from a dropping funnel to 29.78 g. (0.25 mole) of I in 25 ml of methylene dichloride. The reaction proceeded exothermically and was stirred for about 1 hour. In order to bring it to room temperature, the reaction mixture was stirred for an additional hour. After washing with three 25 ml portions of water and drying over Drierite, the organic material was distilled to yield 26 g. (83.4%) of O-isopropyl methyl phosphonofluoridothioate, b. p. 72°–73° C. at 58 mm $n_D^{25}$ 1.4320.

Analysis: Calcd for $C_4 H_{10} FOSP$: C, 30.76; H, 6.45; P, 19.84. Found: C, 30.99; H, 6.50; P, 20.03.

EXAMPLE 4

O-n-BUTYL METHYLPHOSPHONOFLUORIDOTHIOATE

A solution of 19.16 g. (0.26 mole) of n-butanol and of 26.16 g. (0.26 mole) of triethylamine was added from a dropping funnel to 30.0 g. (0.26 mole) of I in 25 ml methylene dichloride. The reaction proceeded exothermically and was stirred for 1 hour. The mixture was stirred an additional hour to bring it to room temperature. After washing with three 25 ml portions of water and drying over Drierite, the organic material was distilled to yield 31.8 g. (72.3%) of O-n-butyl methylphosphonofluoridothioate, b.p. 76°–77.5° C. at 22 mm $n_D^{25}$ 1.4415.

Analysis: Calcd for $C_5 H_{12} FOPS$: C, 35.28; H, 7.11; F, 11.16; P, 18.20; S, 18.84. Found: C, 36.1; H, 7.9; F, 11.13; P, 17.26; S, 18.55.

EXAMPLE 5

O-n-AMYL METHYLPHOSPHONOFLUORIDOTHIOATE

A solution of 22.79 g. (0.26 mole) of n-amyl alcohol and of 26.16 g. (0.26 mole) of triethylamine was added from a dropping funnel to 30.0 g. (0.26 mole) of I in 25 ml methylene dichloride the reaction proceeded exothermically and was stirred for about 1 hour. The mixture was stirred an additional hour to bring it to room temperature. After washing with three 25 ml portions of water and drying over Drierite, the organic material was distilled to yield 30.9 g. (64.9%) of O-n-amyl methyl phosphonofluoridothioate, b.p. 83°–87° C. at 25 mm $n_D^{25}$ 1.4439.

Analysis: Calcd for $C_6H_{16}$ FOPS: C, 39.12; H, 7.66; F, 10.31; P, 16.81; S, 17.41. Found: C, 39.5; H, 7.8; F, 10.32; P, 16.86; S, 18.74.

EXAMPLE 6

O-CYCLOHEXYL METHYL PHOSPHONOFLUORIDOTHIOATE

A solution of 2.0 g. (0.20 mole) of cyclohexanol and 20.2 g. (0.20 mole) of triethylamine was added from a dropping funnel to 23.2 g. (0.20 mole) of I in 25 ml of methylene dichloride. The reaction was treated as above and yielded 33 g. (84.1%) of O-cyclohexyl methylphosphonofluoridothioate b.p. 105° C. at 25 mm $n_D^{25}$ 1.4762.

Analysis: Calcd for $C_7H_{14}$ FOPS: C, 42.84; H, 7.19; P, 15.79; S, 16.35. Found: C, 43.17; H, 7.29; P, 16.04; S, 15.8.

EXAMPLE 7

O-(2-METHYL CYCLOHEXYL) METHYLPHOSPHONOFLUORIDOTHIOATE

A mixture of 21.6 g. (0.188 mole) of 2-methylcyclohexanol and 19.1 g. (0.188 mole) of triethylamine was added dropwise to 21.9 g. (0.188 mole) of I in 25 ml of methylene dichloride. Following the above procedures, 29.9 g. (76.1%) of O-(2-methylcyclohexyl) methylphosphonofluoridothioate, b.p. 103° at 6.2 mm $n_D^{25}$ 1.4720 are obtained.

EXAMPLE 8

O-(3-METHYLCYCLOHEXYL) METHYLPHOSPHONOFLUROIDOTHIOATE

A mixture of 21.6 g. (0.188 mole) of 3-methylcyclohexanol and of 19.1 g. (0.188 mole) of triethylamine was added dropwise to 21.9 g. (0.188 mole) of I in 25 ml of methylene dichloride. After the usual working up, the reaction products were distilled through a two inch Vigereaux column to yield 21.5 g. (54.8%) of trans-O-(3-methylcyclohexyl) methylphosphonofluoridothioate b.p. 103° C. at 10.2 mm $n_D^{25}$ 1.4713 and 6.9 g. (17.6%) of the cis isomer, b.p. 96° C. at 10.0 mm $n_D^{25}$ 1.4705.

EXAMPLE 9

O-(4-METHYLCYCLOHEXYL) METHYL-PHOSPHONOFLUORIDOTHIOANATE

A mixture of 21.6 g. (0.188 mole) of 4-methylcyclohexanol and of 19.1 g. (0.188 mole) of triethylamine was added dropwise to 21.9 g. (0.188 mole) of I in 25 ml of methylene chloride. Following the usual working up, the reaction products were distilled through a 2 inch Vigereaux column to yield 26.2 g. (66.4%) of O-(4-methylcyclohexyl) methyl phosphonofluoridothioate, b.p. 99° C. at 8.2 mm $n_D^{25}$ 1.4700.

EXAMPLE 10

O-(3,3,5-TRIMETHYLCYCLOHEXYL) METHYLPHOSPHONOFLUORIDOTHIOATE

A mixture of 26.7 g. (0.188 mole) of 3,3,5-trimethylcyclohexanol and 19.1 g. (0.188 mole) of triethylamine was added dropwise to 21.9 g. (0.188 mole) of I in 25 ml methylene chloride. Following the usual working up, the reaction products were distilled through a 2 inch Vigereaux column to yield 36.3 g. (82.5%) of O-(3,3,5-trimethylcyclohexyl) methylphosphonofluoridothioate, b.p. 66.5° C. at 0.40 mm $n_D^{25}$ 1.4665.

We claim:

1. A compound having the structure represented by the formula:

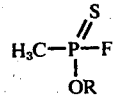

in which R is selected from the group consisting of alkyl groups of 1–5 carbon atoms and cycloalkyl groups of 6–9 carbon atoms.

2. O-isopropyl methylphosphonofluoridothioate.
3. O-cyclohexyl methylphosphonofluoridothioate.
4. Methyl phosphonothioic difluoride.

* * * * *